(12) United States Patent
Mitsumata et al.

(10) Patent No.: US 12,016,920 B2
(45) Date of Patent: Jun. 25, 2024

(54) ADJUVANT BASED ON PEPTIDE NUCLEIC ACID

(71) Applicant: DENKA COMPANY LIMITED, Chuo-ku (JP)

(72) Inventors: Ryotaro Mitsumata, Gosen (JP); Asumi Kanda, Gosen (JP)

(73) Assignee: DENKA COMPANY LIMITED, Chuo-ku (JP)

( * ) Notice: Subject to any disclaimer, the term of this patent is extended or adjusted under 35 U.S.C. 154(b) by 76 days.

(21) Appl. No.: 17/616,490

(22) PCT Filed: Jun. 5, 2020

(86) PCT No.: PCT/JP2020/022293
§ 371 (c)(1),
(2) Date: Dec. 3, 2021

(87) PCT Pub. No.: WO2020/246584
PCT Pub. Date: Dec. 10, 2020

(65) Prior Publication Data
US 2023/0330221 A1  Oct. 19, 2023

(30) Foreign Application Priority Data

Jun. 6, 2019  (JP) .................. 2019-106444

(51) Int. Cl.
*A61K 39/39* (2006.01)
*A61K 39/00* (2006.01)

(52) U.S. Cl.
CPC .... *A61K 39/39* (2013.01); *A61K 2039/55516* (2013.01); *A61K 2039/55561* (2013.01)

(58) Field of Classification Search
CPC .......... C61K 39/39; A61K 2039/55516; A61K 2039/55561; A61K 39/39; C07K 14/003; C07K 14/005; C07K 7/06; C07K 14/47; C07K 7/08; C07K 2319/00; C07K 16/00; C07K 2317/76; C07K 2319/03; C07K 16/18; C07K 14/705; C07K 2319/02; C07K 2317/622; C07K 14/00; C07K 14/82; C07K 19/00; C07K 2317/24; C07K 2319/10; C07K 1/13; C07K 14/001; C07K 14/7051; C07K 2317/21; C07K 2317/34; C07K 2319/30; C07K 14/78; C07K 2317/73; C07K 2317/92; C07K 1/047; C07K 2317/565; C07K 16/30; C07K 2319/33; C07K 14/4702; C07K 2319/60; C07K 1/1077; C07K 14/4703; C07K 16/2803; C07K 2317/52; C07K 2319/50; C07K 16/32; C07K 16/2863; C07K 16/40; C07K 2317/56; C07K 2319/035; C07K 1/22; C07K 2317/33; C07K 2317/55; C07K 5/06026; C07K 7/02; C07K 2317/31; C07K 14/4748; C07K 16/28; C07K 16/2818; C07K 2317/94; C07K 14/195; C07K 16/2809; C07K 2317/77; C07K 2319/01; C07K 2319/21; C07K 1/04; C07K 16/2866; C07K 2319/40; C07K 14/415; C07K 17/08; C07K 2319/20; C07K 5/06139; C07K 14/505; C07K 14/52; C07K 2319/80; C07K 14/525; C07K 14/575; C07K 14/70596; C07K 2317/732; C07K 2319/09; C07K 1/042; C07K 14/435; C07K 16/44; C07K 17/00; C07K 2/00; C07K 7/64; C07K 16/22; C07K 16/2833; C07K 2299/00; C07K 2319/70; C07K 5/0821; C07K 9/00; C07K 1/34; C07K 14/43586; C07K 14/70521; C07K 14/70578; C07K 2317/524; C07K 2317/734; C07K 14/51; C07K 14/545; C07K 14/61; C07K 14/775; C07K 16/2827; C07K 16/2896; C07K 5/06078; C07K 5/0806; C07K 14/43595; C07K 14/70539; C07K 14/7155; C07K 14/7158; C07K 16/2878; C07K 16/2887; C07K 5/0815; C07K 1/02; C07K 14/524; C07K 14/70503; C07K 16/241; C07K 16/3061; C07K 16/3069; C07K 2317/32; C07K 2319/92; C07K 5/06034; C07K 5/081; C07K 5/0812; C07K 5/1008;
(Continued)

(56) References Cited

U.S. PATENT DOCUMENTS 7,947,657 B2 * 5/2011 Tonelli .................... A61P 35/00
                                                          536/23.1
8,206,749 B1  6/2012 O'Hagan et al.
(Continued)

FOREIGN PATENT DOCUMENTS

CN  1533284 A  9/2004
CN  101208431 A  6/2008
(Continued)

OTHER PUBLICATIONS

International Search Report issued Aug. 4, 2020 in PCT/JP2020/022293, 3 pages.
(Continued)

*Primary Examiner* — Bao Q Li
(74) *Attorney, Agent, or Firm* — Oblon, McClelland, Maier & Neustadt, L.L.P.

(57) ABSTRACT

Provided are an adjuvant useful for preparing a vaccine having high efficacy and high safety, and a vaccine composition comprising the adjuvant.
The adjuvant comprises a peptide nucleic acid to which a cell penetrating peptide is bound.

7 Claims, 6 Drawing Sheets
Specification includes a Sequence Listing.

(58) Field of Classification Search
CPC .......... C07K 1/00; C07K 1/08; C07K 14/245;
C07K 14/35; C07K 14/43518; C07K
14/4738; C07K 14/475; C07K 14/55;
C07K 14/62; C07K 14/75; C07K 14/765;
C07K 14/805; C07K 16/005; C07K
16/24; C07K 16/283; C07K 17/14; C07K
2317/14; C07K 2319/43; C07K 2319/74;
C07K 5/0808; C07K 5/1019; C07K 7/00;
C07K 1/023; C07K 14/215; C07K
14/315; C07K 14/4705; C07K 14/4713;
C07K 14/4747; C07K 14/70571; C07K
14/71; C07K 14/7151; C07K 14/8146;
C07K 16/084; C07K 16/244; C07K
16/2851; C07K 16/303; C07K 2317/41;
C07K 2317/526; C07K 2317/54; C07K
2317/569; C07K 2317/64; C07K 2318/20;
C07K 2319/24; C07K 2319/61; C07K
1/14; C07K 14/22; C07K 14/32; C07K
14/38; C07K 14/4721; C07K 14/4732;
C07K 14/4736; C07K 14/605; C07K
14/72; C07K 14/721; C07K 16/2821;
C07K 16/3084; C07K 16/468; C07K
2319/22; C07K 2319/31; C07K 2319/75;
C07K 5/06086; C07K 5/101; C07K
1/026; C07K 14/163; C07K 14/255;
C07K 14/28; C07K 14/34; C07K
14/4716; C07K 14/4746; C07K 14/60;
C07K 14/70517; C07K 14/70575; C07K
16/06; C07K 16/248; C07K 16/46; C07K
2317/22; C07K 2317/40; C07K 2317/522;
C07K 2317/567; C07K 2317/70; C07K
2319/35; C07K 2319/41; C07K 5/0215;
C07K 5/06113; C07K 5/1016; C07K
9/005; C07K 1/20; C07K 1/36; C07K
14/11; C07K 14/15; C07K 14/155; C07K
14/16; C07K 14/205; C07K 14/295;
C07K 14/40; C07K 14/43568; C07K
14/463; C07K 14/4723; C07K 14/4728;
C07K 14/495; C07K 14/515; C07K
14/5431; C07K 14/635; C07K 14/70532;
C07K 14/715; C07K 14/723; C07K
16/10; C07K 16/1242; C07K 16/26;
C07K 16/3076; C07K 16/42; C07K
17/02; C07K 17/04; C07K 17/10; C07K
2317/30; C07K 2317/35; C07K 2317/515;
C07K 2317/626; C07K 2317/71; C07K
2317/75; C07K 2317/90; C07K 2319/036;
C07K 2319/06; C07K 2319/32; C07K
2319/71; C07K 2319/73; C07K 2319/85;
C07K 2319/91; C07K 5/00; C07K
5/06052; C07K 5/0606; C07K 5/06095;
C07K 5/0817; C07K 7/04; C07K 7/14;
C07K 7/54; C07K 1/003; C07K 1/006;
C07K 1/063; C07K 1/1072; C07K
1/1075; C07K 1/306; C07K 14/235;
C07K 14/24; C07K 14/31; C07K 14/37;
C07K 14/39; C07K 14/43531; C07K
14/43545; C07K 14/44; C07K 14/46;
C07K 14/4708; C07K 14/4711; C07K
14/472; C07K 14/521; C07K 14/535;
C07K 14/5428; C07K 14/5434; C07K
14/565; C07K 14/70514; C07K 14/70525;
C07K 14/70535; C07K 14/70542; C07K
14/70564; C07K 14/7153; C07K 14/745;
C07K 16/065; C07K 16/08; C07K
16/081; C07K 16/1009; C07K 16/1027;
C07K 16/12; C07K 16/1214; C07K
16/1228; C07K 16/1232; C07K 16/1271;
C07K 16/1275; C07K 16/16; C07K
16/246; C07K 16/2806; C07K 16/2812;
C07K 16/2836; C07K 16/2869; C07K
16/3007; C07K 16/3046; C07K 16/3053;
C07K 16/462; C07K 2317/10; C07K
2317/51; C07K 2317/53; C07K 2317/72;
C07K 2319/033; C07K 2319/23; C07K
2319/42; C07K 2319/55; C07K 2319/72;
C07K 2319/735; C07K 2319/81; C07K
4/00; C07K 5/06008; C07K 5/06104;
C07K 5/08; C07K 5/1013; C07K 5/1021;
C07K 5/12; C07K 1/06; C07K 1/061;
C07K 1/067; C07K 1/088; C07K 1/10;
C07K 1/113; C07K 1/12; C07K 1/145;
C07K 1/16; C07K 1/165; C07K 1/18;
C07K 1/30; C07K 1/32; C07K 11/00;
C07K 14/01; C07K 14/015; C07K
14/135; C07K 14/161; C07K 14/165;
C07K 14/23; C07K 14/27; C07K 14/33;
C07K 14/36; C07K 14/43504; C07K
14/43522; C07K 14/43536; C07K
14/43563; C07K 14/43572; C07K
14/43581; C07K 14/445; C07K 14/461;
C07K 14/4706; C07K 14/4712; C07K
14/4722; C07K 14/4726; C07K 14/4727;
C07K 14/4733; C07K 14/4741; C07K
14/523; C07K 14/5443; C07K 14/56;
C07K 14/57545; C07K 14/57563; C07K
14/5759; C07K 14/58; C07K 14/585;
C07K 14/665; C07K 14/70; C07K
14/755; C07K 14/76; C07K 14/77; C07K
14/8114; C07K 14/8121; C07K 16/02;
C07K 16/1018; C07K 16/1063; C07K
16/1203; C07K 16/1217; C07K 16/1235;
C07K 16/1292; C07K 16/242; C07K
16/247; C07K 16/2815; C07K 16/2839;
C07K 16/2845; C07K 16/286; C07K
16/2875; C07K 16/2881; C07K 16/2893;
C07K 16/3015; C07K 16/3092; C07K
16/34; C07K 16/36; C07K 16/4208;
C07K 16/4241; C07K 17/06; C07K
2317/20; C07K 2317/23; C07K 2317/624;
C07K 2317/74; C07K 2318/00; C07K
2319/034; C07K 2319/07; C07K 2319/08;
C07K 5/0205; C07K 5/06; C07K 5/0827;
C07K 7/23; C07K 7/56; C07K 9/001;
C07K 9/003; B01J 2219/00722; B01J
19/0046; B01J 2219/00659; B01J
2219/00596; B01J 2219/00605; B01J
2219/00585; B01J 2219/00725; B01J
2219/00612; B01J 2219/00626; B01J
2219/00637; B01J 2219/00527; B01J
2219/0061; B01J 2219/00729; B01J
2219/00608; B01J 2219/00497; B01J
2219/00529; B01J 2219/00576; B01J
2219/00677; B01J 2219/0059; B01J
2219/00711; B01J 2219/005; B01J
2219/0063; B01J 2219/00689; B01J
2219/00432; B01J 2219/0072; B01J
2219/00617; B01J 2219/00641; B01J
2219/00675; B01J 2219/00707; B01J 2219/00621; B01J 2219/00702; B01J
2219/00653; B01J 2219/00695; B01J
2219/00315; B01J 2219/00378; B01J
2219/0074; B01J 2219/00387; B01J
2219/00317; B01J 2219/00635; B01J
2219/00648; B01J 2219/00351; B01J
2219/00536; B01J 2219/00644; B01J
20/3212; B01J 2219/007; B01J 20/286;
B01J 2219/00441; B01J 2219/00533;
B01J 2219/00619; B01J 2219/00731;
B01J 2219/00502; B01J 2219/00547;
B01J 20/3274; B01J 2219/00274; B01J
2219/00511; B01J 2219/0054; B01J
2219/00563; B01J 2219/00592; B01J
20/3204; B01J 20/3251; B01J
2219/00691; B01J 2219/00743; B01J
19/10; B01J 20/3219; B01J 2219/00382;
B01J 2219/00385; B01J 2219/00545;
B01J 2219/00662; B01J 2219/00673;
B01J 2220/54; B01J 19/00; B01J 20/103;
B01J 20/261; B01J 20/285; B01J 20/321;
B01J 20/3293; B01J 2219/00353; B01J
2219/00369; B01J 2219/00416; B01J
2219/00421; B01J 2219/00439; B01J
2219/0052; B01J 2219/00522; B01J
2219/00542; B01J 2219/00554; B01J
2219/00574; B01J 2219/00632; B01J
39/26; B01J 13/04; B01J 20/3242; B01J
20/3255; B01J 20/3282; B01J 20/3285;
B01J 2219/00326; B01J 2219/00333;
B01J 2219/00367; B01J 2219/00448;
B01J 2219/00454; B01J 2219/00463;
B01J 2219/00549; B01J 2219/00572;
B01J 2219/00581; B01J 2219/00628;
B01J 2219/00664; B01J 2219/00668;
B01J 2219/00693; B01J 39/20; B01J
41/20; B01J 19/0093; B01J 19/087; B01J
19/123; B01J 19/127; B01J 19/128; B01J
20/22; B01J 20/24; B01J 20/267; B01J
20/28016; B01J 20/28033; B01J
20/28085; B01J 20/281; B01J 20/283;
B01J 20/287; B01J 20/327; B01J 21/06;
B01J 21/18; B01J 2219/00295; B01J
2219/00299; B01J 2219/00308; B01J
2219/00344; B01J 2219/00358; B01J
2219/00427; B01J 2219/0043; B01J
2219/00461; B01J 2219/00466; B01J
2219/00468; B01J 2219/00495; B01J
2219/00504; B01J 2219/00515; B01J
2219/00524; B01J 2219/00551; B01J
2219/0056; B01J 2219/00567; B01J
2219/00569; B01J 2219/00599; B01J
2219/00603; B01J 2219/00646; B01J
2219/00686; B01J 2219/00736; B01J
2219/085; B01J 2219/0892; B01J
2220/80; B01J 23/745; B01J 27/24; B01J
35/004; B01J 19/008; B01J 19/121; B01J
2/04; B01J 2/06; B01J 2/08; B01J
20/0229; B01J 20/06; B01J 20/265; B01J
20/28009; B01J 20/28014; B01J
20/28092; B01J 20/28097; B01J 20/289;
B01J 20/3057; B01J 20/3078; B01J
20/3085; B01J 20/3217; B01J 20/3253;
B01J 20/3272; B01J 20/3276; B01J
20/3278; B01J 2219/00011; B01J
2219/00162; B01J 2219/00272; B01J
2219/00313; B01J 2219/00328; B01J
2219/00364; B01J 2219/00371; B01J
2219/00479; B01J 2219/00594; B01J
2219/00666; B01J 2219/00704; B01J
2219/00734; B01J 2219/00756; B01J
39/04; B01J 39/07; B01J 41/04; B01J
43/00; B01J 13/0034; B01J 13/0043;
B01J 13/02; B01J 13/043; B01J 13/14;
B01J 13/18; B01J 13/185; B01J 19/16;
B01J 20/08; B01J 20/28004; B01J
20/28007; B01J 20/28019; B01J
20/28028; B01J 20/28035; B01J
20/28054; B01J 20/28057; B01J
20/28061; B01J 20/28078; B01J
20/28083; B01J 20/282; B01J 20/30;
B01J 20/3042; B01J 20/3064; B01J
20/3071; B01J 20/3092; B01J 20/32;
B01J 20/3208; B01J 20/3225; B01J
20/3234; B01J 20/3236; B01J 20/3257;
B01J 20/3259; B01J 20/3289; B01J
20/3295; B01J 21/063; B01J 21/12; B01J
2219/00319; B01J 2219/0036; B01J
2219/00389; B01J 2219/00425; B01J
2219/00436; B01J 2219/00452; B01J
2219/00509; B01J 2219/00623; B01J
2219/00639; B01J 2219/00655; B01J
2219/0068; B01J 2219/00698; B01J
2219/00709; B01J 2219/00713; B01J
2219/00716; B01J 2219/00783; B01J
2219/00831; B01J 2219/0086; B01J
2219/00891; B01J 2219/00912; B01J
2219/00934; B01J 2219/00957; B01J
2219/00968; B01J 2219/0097; B01J
2219/0099; B01J 2219/089; B01J
2220/58; B01J 2220/82; B01J 23/002;
B01J 23/30; B01J 23/52; B01J 23/8906;
B01J 2523/00; B01J 2523/15; B01J
2523/41; B01J 2523/51; B01J 2523/69;
B01J 2531/005; B01J 2531/025; B01J
2531/23; B01J 2531/26; B01J 2531/27;
B01J 2531/28; B01J 2531/36; B01J
2531/37; B01J 2531/38; B01J 2531/72;
B01J 2531/842; B01J 2531/845; B01J
2531/847; B01J 2531/96; B01J 27/188;
B01J 31/0254; B01J 31/061; B01J
31/127; B01J 31/1658; B01J 31/1805;
B01J 31/1815; B01J 31/26; B01J
35/0013; B01J 35/002; B01J 35/0033;
B01J 35/006; B01J 37/0205; B01J
37/0209; B01J 37/0215; B01J 37/04;
B01J 37/16; B01J 37/343; B01J 37/344;
B01J 4/02; B01J 41/07; B01J 41/14;
Y10T 436/143333; Y10T 436/24; Y10T
436/25; Y10T 428/2982; Y10T 436/2575;
Y10T 436/11; Y10T 436/25375; Y10T
428/2984; Y10T 428/2991; Y10T 436/10;
Y10T 436/17; Y10T 436/2525; Y10T
428/2998; Y10T 428/31768; Y10T
436/101666; Y10T 436/255; Y10T
428/31504; Y10T 436/14555; Y10T
436/13; Y10T 436/105831; Y10T
436/172307; Y10T 436/20; Y10T 156/19;
Y10T 428/249953; Y10T 436/142222;
Y10T 436/147777; Y10T 428/249991;

Y10T 436/107497; Y10T 436/110833;
Y10T 436/113332; Y10T 436/144444;
Y10T 156/10; Y10T 428/24802; Y10T
428/249992; Y10T 428/249993; Y10T
428/2995; Y10T 428/31612; Y10T
428/31663; Y10T 428/31667; Y10T
428/31786; Y10T 428/31938; Y10T
428/31942; Y10T 436/14; Y10T 436/16;
Y10T 442/10; Y10T 156/1062; Y10T
428/12431; Y10T 428/24479; Y10T
428/249924; Y10T 428/249925; Y10T
428/249928; Y10T 428/24994; Y10T
428/249952; Y10T 428/24999; Y10T
428/25; Y10T 428/2933; Y10T 428/294;
Y10T 428/2958; Y10T 428/2964; Y10T
428/2975; Y10T 428/298; Y10T
428/2989; Y10T 428/30; Y10T
428/31678; Y10T 428/31844; Y10T
428/31935; Y10T 428/31971; Y10T
436/103332; Y10T 436/106664; Y10T
436/112499; Y10T 436/114165; Y10T
436/114998; Y10T 436/117497; Y10T
436/118339; Y10T 436/173076; Y10T
436/201666; Y10T 436/206664; Y10T
436/21; Y10T 436/23; Y10T 29/49716;
Y10T 428/13; Y10T 428/1393; Y10T
428/24612; Y10T 428/24628; Y10T
428/249921; Y10T 428/268; Y10T
428/2938; Y10T 428/2993; Y10T
428/2996; Y10T 428/31507; Y10T
428/31515; Y10T 428/31518; Y10T
428/31536; Y10T 428/31551; Y10T
428/31725; Y10T 428/32; Y10T 442/60;
C03C 17/30; C03C 17/3405; C03C 1/04;
C03C 11/00; C03C 12/00; C03C 14/00;
C03C 14/004; C03C 15/00; C03C 17/006;
C03C 17/007; C03C 17/04; C03C 17/22;
C03C 17/28; C03C 17/42; C03C 2201/32;
C03C 2201/80; C03C 2214/05; C03C
2214/16; C03C 2214/30; C03C 2217/42;
C03C 2217/425; C03C 2218/114; C03C
2218/119; C03C 2218/31; C03C 23/00;
C03C 3/06; C03C 3/064; C03C 4/0007;
C03C 4/08; C03C 8/14; C03C 8/16;
B01L 3/502761; B01L 2300/0636; B01L
2300/0816; B01L 3/5027; B01L
2300/0645; B01L 2400/0487; B01L
3/502715; B01L 2300/0887; B01L
2300/0819; B01L 2300/0822; B01L
2400/0421; B01L 2200/16; B01L
2200/0668; B01L 2200/12; B01L
3/502707; B01L 7/52; B01L 2300/0681;
B01L 2300/0864; B01L 3/50273; B01L
2200/0647; B01L 2200/10; B01L
2300/0877; B01L 2300/087; B01L
2300/16; B01L 2300/0627; B01L
2400/0415; B01L 3/5025; B01L
2200/0652; B01L 2300/0829; B01L
2300/0867; B01L 2300/0896; B01L
3/502784; B01L 2300/12; B01L
2300/161; B01L 3/502; B01L 2300/0654;
B01L 9/527; B01L 2200/025; B01L
2200/663; B01L 2300/042; B01L
2300/0883; B01L 2400/0481; B01L
2400/086; B01L 3/508; B01L 2200/0689;
B01L 2300/046; B01L 2300/0609; B01L
2300/0663; B01L 2300/1827; B01L
2400/043; B01L 3/502738; B01L
3/502753; B01L 3/5085; B01L 2300/089;
B01L 2300/123; B01L 2400/0418; B01L
3/5055; B01L 3/50825; B01L 3/50853;
B01L 3/5088; B01L 2200/0673; B01L
2300/0851; B01L 2300/0861; B01L
2400/0406; B01L 2400/049; B01L
2400/0677; B01L 3/0268; B01L
3/502776; B01L 3/5082; B01L 3/50851;
B01L 2300/021; B01L 2300/0809; B01L
2400/0424; B01L 2200/0631; B01L
2300/023; B01L 2300/1822; B01L
2400/0409; B01L 3/502792; B01L
3/50857; B01L 9/52; B01L 2200/026;
B01L 2200/027; B01L 2200/0684; B01L
2300/041; B01L 2300/047; B01L
2300/0893; B01L 2400/0633; B01L 3/50;
B01L 2200/028; B01L 2200/0642; B01L
2300/02; B01L 2300/069; B01L
2300/0874; B01L 2300/165; B01L
2300/166; B01L 2300/168; B01L
2400/0403; B01L 2400/0442; B01L
2400/0475; B01L 2400/0655; B01L
2400/0683; B01L 3/0244; B01L 3/0293;
B01L 3/5023; B01L 3/523; B01L 9/523;
B01L 2200/021; B01L 2200/04; B01L
2200/0621; B01L 2200/0636; B01L
2200/142; B01L 2200/185; B01L
2300/045; B01L 2300/0806; B01L
2300/0825; B01L 2300/0832; B01L
2300/126; B01L 2300/163; B01L
2400/06; B01L 2400/0638; B01L
3/502746; B01L 3/505; B01L 7/00; B01L
2200/0678; B01L 2200/14; B01L
2200/147; B01L 2300/024; B01L
2300/025; B01L 2300/06; B01L
2300/0858; B01L 2300/10; B01L
2300/1838; B01L 2300/1877; B01L
2300/1894; B01L 2400/02; B01L
2400/0439; B01L 2400/0451; B01L
2400/0454; B01L 2400/0457; B01L
2400/0605; B01L 2400/0611; B01L
3/021; B01L 3/0248; B01L 3/0275; B01L
3/0289; B01L 3/502769; B01L 3/545;
B01L 3/5453; B01L 7/525; B01L 9/00;
B01L 9/56; B01L 2200/143; B01L
2200/148; B01L 2300/022; B01L
2300/04; B01L 2300/043; B01L
2300/0803; B01L 2300/0838; B01L
2300/0848; B01L 2300/088; B01L
2300/14; B01L 2400/027; B01L
2400/0622; B01L 2400/0666; B01L
2400/0688; B01L 2400/084; B01L
2400/088; B01L 3/00; B01L 3/0262;
B01L 3/5021; B01L 3/5029; B01L
3/50855; B01L 3/567; A61P 35/00; A61P
43/00; A61P 29/00; A61P 25/00; A61P
25/28; A61P 9/00; A61P 31/00; A61P
31/12; A61P 3/10; A61P 31/04; A61P
9/10; A61P 21/00; A61P 19/02; A61P
37/02; A61P 3/00; A61P 13/12; A61P
1/16; A61P 17/00; A61P 11/00; A61P
3/04; A61P 37/06; A61P 37/04; A61P

37/00; A61P 25/16; A61P 1/04; A61P
17/02; A61P 27/02; A61P 1/00; A61P
21/04; A61P 31/18; A61P 25/14; A61P
17/06; A61P 7/00; A61P 11/06; A61P
35/02; A61P 3/06; A61P 19/00; A61P
37/08; A61P 21/02; A61P 15/00; A61P
25/08; A61P 25/18; A61P 9/12; A61P
31/14; A61P 25/02; A61P 25/24; A61P
19/08; A61P 31/20; A61P 19/10; A61P
7/06; A61P 9/04; A61P 31/10; A61P
33/00; A61P 35/04; A61P 7/02; A61P
7/04; A61P 25/04; A61P 25/30; A61P
5/00; A61P 25/22; A61P 39/06; A61P
25/20; A61P 27/16; A61P 31/22; A61P
13/00; A61P 13/02; A61P 31/16; A61P
33/02; A61P 1/02; A61P 13/08; A61P
19/04; A61P 5/14; A61P 17/14; A61P
1/18; A61P 13/10; A61P 17/04; A61P
3/14; A61P 27/06; A61P 27/12; A61P
3/08; A61P 25/32; A61P 9/06; A61P
33/06; A61P 15/10; A61P 17/08; A61P
9/08; A61P 1/14; A61P 15/08; A61P
19/06; A61P 5/06; A61P 39/00; A61P
11/02; A61P 29/02; A61P 31/06; A61P
9/14; A61P 3/02; A61P 39/02; A61P 9/02;
A61P 5/50; A61P 17/16; A61P 17/18;
A61P 27/00; A61P 41/00; A61P 11/08;
A61P 5/16; A61P 7/08; A61P 17/12;
A61P 11/10; A61P 11/14; A61P 25/06;
A61P 27/10; A61P 1/12; A61P 27/04;
A61P 3/12; A61P 5/48; A61P 7/10; A61P
1/10; A61P 11/16; A61P 15/04; A61P
15/12; A61P 23/00; A61P 23/02; A61P
25/36; A61P 27/14; A61P 5/18; A61P
17/10; A61P 25/26; A61P 33/14; A61P
39/04; A61P 5/38; A61P 5/44; A61P 1/06;
A61P 11/04; A61P 13/06; A61P 5/22;
A61P 5/24; A61P 5/46; A61P 1/08; A61P
21/06; A61P 25/10; A61P 31/02; A61P
33/04; A61P 5/10; A61P 5/42; C12N
2310/3181

See application file for complete search history.

(56) References Cited

U.S. PATENT DOCUMENTS

| 9,562,228 | B2* | 2/2017 | Brown ............... A61P 35/00 |
| 9,895,448 | B2* | 2/2018 | Manoharan ........ C12N 15/1137 |
| 9,902,973 | B2* | 2/2018 | Van Der Oost ...... C12N 15/102 |
| 10,125,361 | B2* | 11/2018 | May ............... A61K 47/6455 |
| 2016/0206715 | A1 | 7/2016 | Theriault et al. |
| 2018/0015174 | A1 | 1/2018 | Irvine et al. |

FOREIGN PATENT DOCUMENTS

| EP | 1 279 404 A1 | 1/2003 |
| JP | 2002-537102 A | 11/2002 |
| JP | 2016-515538 A | 5/2016 |
| WO | WO 2006/110760 A2 | 10/2006 |

OTHER PUBLICATIONS

Takayama, Noriko et al., "Activation of mucous immunity by transnasal administration of CpG-ODN using SPG-R8", Drug Delivery System, 2007, vol. 22, No. 3, pp. 395.

Bae, H. D. et al., "Potential of translationally controlled tumor protein-derived protein transduction domains as antigen carriers for nasal vaccine delivery", Mol. Pharmaceutics, 2016, vol. 13, pp. 3196-3205.

Marichal, T, et al., "DNA released from dying host cells mediates aluminum adjuvant activity", Nat Med., 2011; 17(8): pp. 1-8 and cover page.

Office Action and Search Report issued on May 24, 2023 for Chinese Patent Application No. 202080041821.3 (with machine translation) 16 pages.

Extended European Search Report issued May 8, 2023 in European Patent Application No. 20817766.7, 10 pages.

Takehiko Shiraishi, et al., "Enhanced delivery of cell-penetrating peptide-peptide nucleic acid conjugates by endosomal disruption," Nature Protocols, vol. 1, No. 2, XP008119593, 2006, 4 pages.

John J. Turner, et al., "RNA targeting with peptide conjugates of oligonucleotides, siRNA and PNA," Blood Cells, Molecules, and Diseases, vol. 38, XP005733323, 2007, 7 pages.

Sun-Je Woo, et al., "Co-administration of carcinoembryonic antigen and HIV TAT fusion protein with CpG-oligodeoxynucleotide induces potent antitumor immunity," Cancer Science, vol. 99, No. 5, XP93042496, May 2008, pp. 1034-1039.

* cited by examiner

ADJUVANT BASED ON PEPTIDE NUCLEIC ACID

TECHNICAL FIELD

The present invention relates to a peptide nucleic acid in which a cell penetrating peptide having an immunostimulatory capability is modified.

BACKGROUND ART

An acquired immune system has a capability of forming an immune memory which enables a once experienced foreign substance to be dealt with quickly in second and subsequent exposures. It is a vaccine that takes advantage of the immune memory, and by inoculation of a vaccine, immunity capable of neutralizing a pathogen can be obtained before exposure to the pathogen.

Approved vaccines include live attenuated vaccines, inactivated vaccines, and subunit vaccines such as purified recombinant proteins, and in particular, live attenuated vaccines are vaccines having high efficacy, but have infectivity and are therefore difficult to make safe reliably, so that there is a concern about unexpected side reactions. On the other hand, inactivated vaccines and subunit vaccines are vaccines superior in safety to live attenuated vaccines, but lose infectivity and therefore lack capability of generating natural immunity, so that it is not possible to impart sufficient acquired immunity with an antigen alone. Thus, many of approved inactivated vaccines and subunit vaccines are preparations in which an adjuvant having an immunostimulatory capability is added to an antigen. Therefore, in development of a vaccine having high safety, an inactivated vaccine or subunit vaccine antigen having high safety should be used, and addition of an adjuvant having an immunostimulatory capability is required for acquiring sufficient efficacy.

For enhancing the protective effect against infection of a pathogen, immunity induction in the mucosal membrane as a gate for invasion of a pathogen is also important. Immunity induction in the mucosal membrane is achieved by administration of a mucosal vaccine. Approved mucosal vaccines are live attenuated vaccines or toxin-derived vaccines having mucosal affinity, and immunity sufficient for protection against infection is difficult to generate with inactivated vaccines or subunit vaccines which have no mucosal affinity. Thus, an adjuvant which enhances mucosal immunity is required even in mucosal administration of such antigens.

Examples of the adjuvant used in approved vaccines include aluminum salts and squalene-based emulsions, and few adjuvants are approved, and aluminum salts are known to promote IgE induction (Non Patent Literature 1). The above-described adjuvants are adjuvants for injection preparations, and are difficult to combine with mucosal vaccines.

On the other hand, a peptide nucleic acid (PNA) which is a modified nucleic acid obtained by converting a sugar-phosphate backbone of a nucleic acid into a N-(2-aminoethyl)glycine backbone has a high duplex formation capability, is not degraded by nucleases in the body, and is therefore expected to be applied as an antisense molecule and the like.

In the field of drug delivery and the like, as a technique for introducing a protein, a peptide or a low-molecular compound into cells to function therein, a cell penetrating peptide (CPP) is bound to such a molecule.

However, it is not known that PNA, or PNA to which CPP is bound is used as an adjuvant.

CITATION LIST

Non Patent Literature

Non Patent Literature 1: Marichal T, Ohata K, Bedoret D, Mesnil C, Sabatel C, Kobiyama K, Lekeux P, Coban C, Akira S, Ishii K J, Bureau F, Desmet C J. DNA released from dying host cells mediates aluminum adjuvant activity. Nat Med. 2011 Jul. 17; 17(8): 996-1002.

SUMMARY OF INVENTION

Technical Problem

The present invention relates to a provision of an adjuvant useful for preparation of a vaccine having high efficacy and high safety, and a vaccine composition comprising the adjuvant.

Solution to Problem

The present inventors extensively conducted studies, and resultantly found that when a peptide nucleic acid is modified with a cell penetrating peptide (CPP) such as TAT (trans-activator of transcription protein) of HIV (human immunodeficiency virus), the peptide nucleic acid to which CPP is bound has adjuvant activity in both of injection and mucosal administration.

Specifically, the present invention relates to the following 1) to 6).

1) An adjuvant comprising a peptide nucleic acid to which a cell penetrating peptide is bound.
2) An adjuvant composition comprising: a peptide nucleic acid to which a cell penetrating peptide is bound; and a pharmaceutically acceptable carrier.
3) A vaccine composition comprising the adjuvant according to 1), and an antigen.
4) Use of a peptide nucleic acid to which a cell Penetrating peptide is bound, for producing an adjuvant.
5) Use as an adjuvant of a peptide nucleic acid to which a cell penetrating peptide is bound.
6) A method for using as an adjuvant a peptide nucleic acid to which a cell penetrating peptide is bound.

Advantageous Effect of Invention

According to the present invention, the efficacy of an inactivated vaccine having high safety can be enhanced, and it is possible to significantly contribute to the pharmaceutical industry by developing a prophylactic drug with high quality.

DESCRIPTION OF EMBODIMENTS

Hereinafter, preferred embodiments of the present invention will be described in detail. However, the present invention is not limited to the embodiments below.

In the present invention, the term "peptide nucleic acid to which a cell penetrating peptide is bound" means a molecule in which a peptide nucleic acid is bound to the N- or C-terminal of a cell penetrating peptide, and this peptide nucleic acid is also referred to as Mitsumata-immunostimulatory peptide nucleic acid (MIP) herein.

The term "cell penetrating peptide (CPP)" refers to a peptide which moves into cells through the cell membrane when coexisting with the cells. Examples thereof include, but are not limited to, peptides derived from TAT of HIV, penetratin derived from Antennapedia of Drosophila, polvarginine, transportan derived from neuropeptide galanin, Pep-1 derived from a nuclear localization signal (NLS) of SV40, and antimicrobial peptide LL37 as shown in Table 1.

A peptide derived from TAT (peptide consisting of the amino acid sequence set forth as SEQ ID NO: 1) is preferable.

The term "peptide nucleic acid (PNA)" refers to a nucleic acid analog having a backbone in which a sugar-phosphate backbone of a nucleic acid is replaced by N-(2-aminoethyl) glycine, and a base is linked via a methylene carbonyl bond. The base in the peptide nucleic acid for use in the present invention may be any of adenine, guanine, thymine, cytosine and uracil, and the chain length is desirably a common chain length of 20 mer or less, but from the viewpoint of adjuvant activity, the chain length is preferably from 3 to 12 mer, and more preferably from 3 to 10 mer.

A structure of a peptide nucleic acid of 3 to 12 mer is shown in formula (1) below:

(1)

wherein Bases may be the same or different, and each represents adenine, guanine, thymine, cytosine or uracil, R represents —COCH or —CONH$_2$, and n represents an integer of 1 to 10.

In the present invention, examples of preferred peptide nucleic acids include peptide nucleic acids of 3 mer or 10 mer which have at least one guanine or cytosine as bases; peptide nucleic acids of 3 mer which have three guanines as bases (G3PNA); peptide nucleic acids of 3 mer which have three cytosines as bases (C3PNA); and peptide nucleic acids of 10 mer which have ten cytosines as bases (C10PNA).

The MIP of the present invention can be produced by linking a peptide nucleic acid to the N- or C-terminal of a cell penetrating peptide using a chemical method, for example, by covalently linking the N-terminals of the cell penetrating peptide to the peptide nucleic acid via a cross-linking agent having N-hydroxysuccinimide ester at both ends.

The peptide nucleic acid can be synthesized by a solid-phase peptide synthesis method known in the art using, for example, a Fmoc-type PNA monomer unit.

TABLE 1

| Peptide | Origin | Sequence (N-terminal → C-terminal) |
| --- | --- | --- |
| TAT (48-60) | HIV TAT protein | GRKKRRQRRRPPQ (SEQ ID NO: 1) |
| Penetratin | Drosophila Antennapedia | RQIKIWFQNRRMKWKK (SEQ ID NO: 2) |
| Polyarginine (R8) | Synthetic peptide | RRRRRRRR (SEQ ID NO: 3) |
| Polyargininc (R9) | Synthetic peptide | RRRRRRRRR (SEQ ID NO: 4) |
| Transportan | Neuropeptide Galanin | GWTLNSAGYLLGKINLKALAALAKKIL (SEQ ID NO: 5) |
| Pep-1 | SV40 NLS | KETWWETWWTEWSQPKKRKV (SEQ ID NO: 6) |
| LL-37 | Antimicrobial peptide | LLGDFERKSKEKIGKEFKRIVQRIKDFLRNLVPRTESC (SEQ ID NO: 7) |

Examples of preferred MIPs for use in the present invention include MIP01 in which the C-terminal of a peptide consisting of 13 amino acids and derived from TAT of HIV (SEQ ID NO: 1) is covalently bound to G3PNA (formula (2)) and MIP03 in which the C-terminal of the peptide is covalently bound to C10PNA (formula (3)) as shown below.

(2)

(3)

As described in Examples below, when a vaccine composition prepared by mixing MIP01 of formula (2) and an influenza antigen (split antigen) is injected into or transmucosally administered to mice, the blood antibody titer with respect to the antigen becomes higher as compared to that in a MIP-free group. In the case of the transmucosal administration, the titer of IgA in the mucosal membrane also increases. MIP03 of formula (3) is shown to have a NFκB-activation capability and a high capability of inducing IL-1β, and is therefore likely to promote activation of the natural immune system. NIP is thus considered to be an adjuvant having a capability of activating natural immunity.

That is, MIP has adjuvant activity which enhances the antibody inducing capability in the blood or the mucosal membrane regardless of whether the antigen is injected or transmucosally administered. Therefore, MIP can be an adjuvant, and a composition containing MIP and a pharmaceutically acceptable carrier can be an adjuvant composition. MIP can be used for producing an adjuvant or an adjuvant composition.

In the present invention, the term "adjuvant" means a substance which increases an immune response to an antigen when the antigen is injected or transmucosally administered.

Here, the term "mucosal membrane" refers to an inner wall particularly of a luminal organ communicating with the outside, such as a digestive organ, a respiratory organ, a urogenital organ or an eye in vertebrates. Thus, examples of the transmucosal administration include, but are not limited to, oral administration, nasal administration (transnasal administration), buccal administration, intravaginal administration, upper respiratory administration, alveolar administration and eye drop administration.

The adjuvant or the adjuvant composition of the present invention can be administered in combination with an antigen, and may be administered simultaneously with the administration of the antigen, or before or after the administration of the antigen.

The dosage of the adjuvant or the adjuvant composition of the present invention can be appropriately determined according to an administration target, an administration method, an administration form and a type of antigen.

The adjuvant of the present invention can be combined with an antigen to form a vaccine composition. The vaccine composition of the present invention can be prepared by mixing an antigen with MIP, and further, an appropriate preparation can be formed by appropriately adding a pharmaceutically acceptable carrier. In the vaccine composition of the present invention, NIP may be chemically bound to an antigen or other ingredients, or may be present as free molecules.

The antigen is a natural product purified from a pathogen, or a protein or a peptide artificially prepared by a method such as gene recombination, and specific examples thereof include virions which are complete viral particles, incomplete viral particles, viral structural proteins, viral non-structural proteins, pathogenic bacterial whole cells, proteins or sugar proteins derived from pathogenic bacteria, infection-protecting antigens and neutralizing epitopes. The antigens include those having infectivity and those losing infectivity (inactivated antigens). Examples of the inactivated antigen include, but are not limited to, those inactivated by operations such as physical operations (X-ray irradiation, UV irradiation, heat and ultrasonic waves) and chemical operations (formalin, beta-propiolactone, binary ethyleneimine, mercury, alcohol and chlorine). It is desirable that the antigens derived from pathogens be inactivated antigens derived from the above-described viruses or pathogenic bacteria from the viewpoint of safety.

Examples of the virus include measles viruses, rubella viruses, mumps viruses, polioviruses, rotaviruses, noroviruses, adenoviruses, enteroviruses, herpesviruses, chickenpox viruses, severe acute respiratory syndrome (SARS) viruses, human immunodeficiency viruses (HIV), human T-cell leukemia viruses (HTLV-1), human papillomaviruses, Japanese encephalitis viruses, West Nile viruses, yellow fiver viruses, dengue viruses, Zika viruses, hepatitis A viruses, hepatitis B viruses, hepatitis C viruses, hepatitis E viruses, RS viruses and influenza viruses, and influenza viruses are preferable.

Examples of the pathogenic bacteria include *Corynebacterium diphtheriae, Clostridium tetani, Bordetella pertussis*, meningococcus, haemophilus influenza B, pneumococci, cholera bacilli, *Mycobacterium tuberculosis* and periodontal disease bacteria.

Examples of the dosage form of the vaccine composition include solutions, suspensions and freeze-dried preparations. Examples of the solution include those obtained by dissolving the vaccine composition in purified water or a buffer solution. Examples of the suspension include those obtained by suspending the vaccine composition in purified water, a buffer solution or the like together with methyl cellulose, hydroxymethyl cellulose, polyvinylpyrrolidone, gelatin, casein or the like.

To these preparations, an absorption promotor, a surfactant, a preservative, a stabilizer, a desiccant, a solubilizer and the like which are typically used can be appropriately added.

The vaccine composition of the present invention may contain an adjuvant other than MIP as long as the immunogenicity and the safety of the vaccine are not impaired.

The amount of the antigen contained in the vaccine composition of the present invention is not particularly limited as long as it is sufficient for inducing a specific antibody response, and the amount of the antigen can be appropriately set also in consideration of the ratio to MIP used in combination. For example, when as the antigen, a split antigen of an influenza virus is used, the dose of the antigen per administration may be in the range of 1 to 60 μg HA (calculated on a HA basis), and is more preferably from 9 to 15 μg HA (calculated on a HA basis). The concentration is a value obtained by measuring the concentration of HA protein by a test method established under the WHO standard or the national standard, such as a single radial immunodiffusion test method.

The administration route of the vaccine composition of the present invention is not particularly limited, and may be any of administration by injection (subcutaneous administration, intramuscular administration, intracutaneous administration and intravenous administration), oral administration, and parenteral administration (e.g. nasal administration, eye drop administration, transvaginal administration, sublingual administration and transcutaneous administration), and for example, the vaccine composition is dropped, nebulized, or sprayed into the nasal cavity to be administered.

Examples of the administration target of the adjuvant composition or the vaccine composition of the present invention include humans, and mammals other than humans, and humans are preferable. Examples of the mammals other than humans include mice, rats, hamsters, guinea pigs, rabbits, pigs, cattle, goats, sheep, dogs, cats, rhesus macaques, cynomolgus monkeys, orangutans and chimpanzees.

EXAMPLES

Hereinafter, the present invention will be described in detail by way of Examples, which should not be construed as limiting the present invention.

<CPP and MIP>

Synthesis of =01 (TAT-derived peptide (SEQ ID NO: 1) as CPP, and MIP01 of formula (2) and MIP03 of formula (3) as MIP was outsourced to Peptide Institute, Inc.

Example 1: Evaluation of Adjuvant Activity in Subcutaneous Administration of MIP01

Each of the undiluted solutions of A/H1N1 subtype (A/Singapore/GP1908/2015 strain) and B/Victoria lineage (B/Maryland/15/2016 strain) of the influenza HA vaccine "SEIKEN" was employed as a split antigen (SV), and the split antigens were mixed in such a manner that the content of hemagglutinin of each strain was 1 μg per 0.3 mL. To the mixture, a cell penetrating peptide consisting of 13 amino acids derived from TAT of HIV or MIP01 was added in an amount of 1 μg. An adjuvant-free administration solution containing the antigen alone was also prepared as a control.

The administration solutions prepared as described above (Table 2) were each subcutaneously administered in an amount of 0.3 mL to the dorsal part of a BALB/c mouse (female, five-week-old) twice at an interval of three weeks (five mice per group), and the whole blood was collected two weeks after each administration. The blood obtained by the collection of the whole blood was centrifuged to prepare serum, and the titer of serum IgG which specifically binds to A/Singapore/GP1908/2015 strain and B/Maryland/15/2016 strain (total IgG) was measured. The neutralizing antibody titer against A/Singapore/GP1908/2015 strain was also measured in the serum after the second administration.

TABLE 2

| # | Antigen Subtype/ lineage | Dose (μgHA/strain/shot) | Adjuvant Name | Sequence (N-terminal → C-terminal) | Dose (μg/shot) |
|---|---|---|---|---|---|
| 1 | A/H1N1 | 1 | CPP01 | GRKKRRQRRRPPQ | 1 |
| 2 | A/H1N1 | 1 | MIP01 | GRKKRRQRRRPPQ-G3PNA | 1 |
| 3 | A/H1N1 | 1 | — | — | — |
| 4 | B/Victoria | 1 | CPP01 | GRKKRRQRRRPPQ | 1 |
| 5 | B/Victoria | 1 | MIP01 | GRKKRRQRRRPPQ-G3PNA | 1 |
| 6 | B/Victoria | 1 | — | — | — |

Figure 1A:
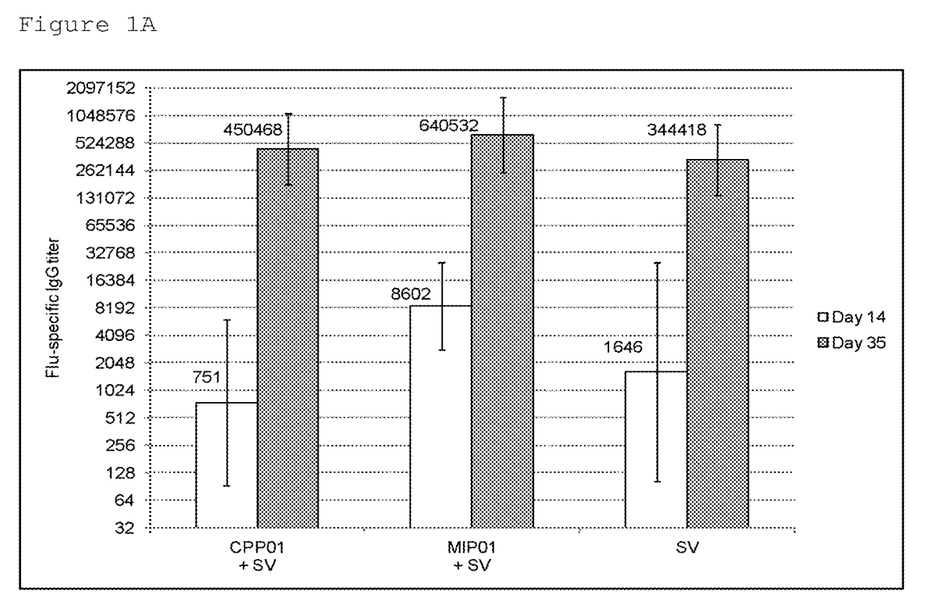
FIG. 1A shows an IgG antibody titer against A/Singapore/GP1908/2015 strain in subcutaneous administration.
Figure 1B:
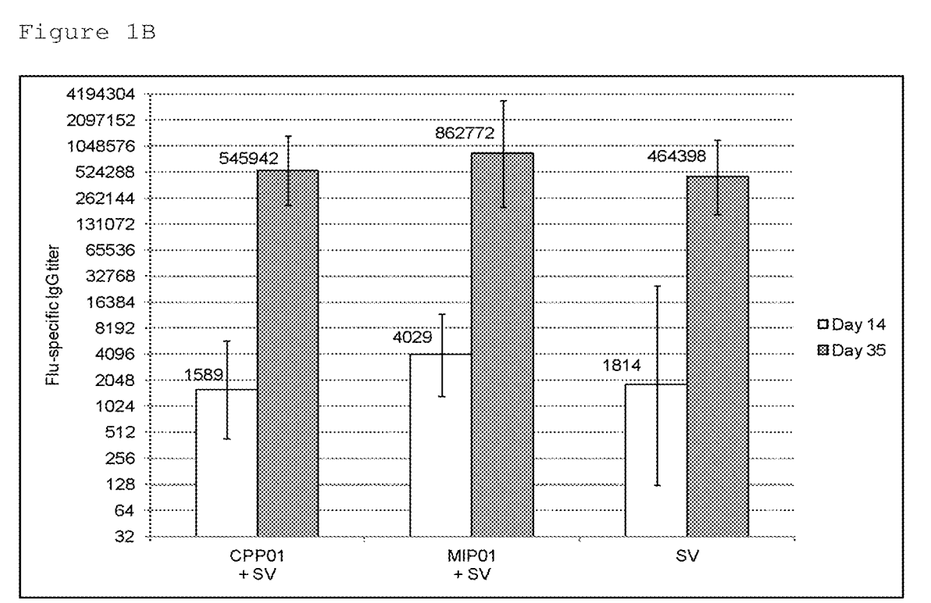
FIG. 1B shows an IgG antibody titer against B/Maryland/15/2015 strain in subcutaneous administration.
Figure 2:
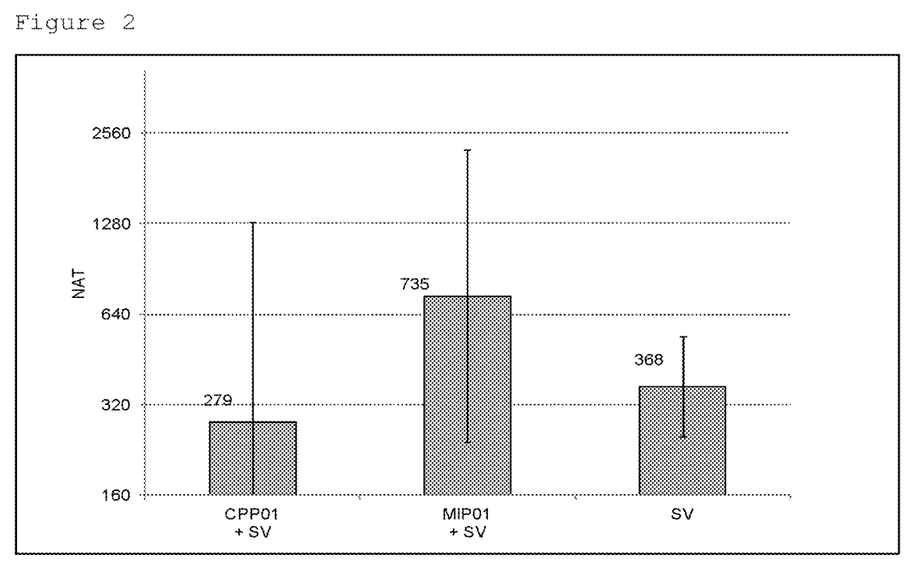
FIG. 2 shows a neutralizing antibody titer against A/Singapore/GP1908/2015 strain on Day 35 in subcutaneous administration.

The IgG titers in each of the administration groups are as shown in FIGS. 1A and 1B. By adding MIP01 to the split antigen in an amount of 1 μg per administration, the blood antigen-specific IgG titer against each strain was made higher as compared to that in the adjuvant-free group in both the first and second administrations. As compared to the CPP01 administration group, the MIP01 administration group showed a higher blood antigen-specific IgG titer against each strain in both the first and second administrations. FIG. 2 shows neutralizing antibody titers against A/Singapore/GP1908/2015 strain after the second administration, and reveals that for the neutralizing antibody titer, the MIP01 administration group showed the highest value, the adjuvant-free group showed the next-highest value, and the CPP01 administration group showed the lowest value. Therefore, administration of MIP01 was confirmed to improve not only the blood antigen-specific IgG titer but also the neutralizing antibody titer important for elimination of viruses, and a structure in which a peptide nucleic acid is bound to a cell penetrating peptide was considered to be important for exhibition of adjuvant activity of MIP01.

Example 2: Evaluation of Adjuvant Activity in Transnasal Administration of MIP01

As in Example 1, each of the undiluted solutions of A/H1N1 subtype (A/Singapore/GP1908/2015 strain) and B/Victoria lineage (B/Maryland/15/2016 strain) of the influenza HA vaccine "SEIKEN" was employed as a split antigen, and the split antigens were mixed in such a manner that the content of hemagglutinin of each strain was 1 vg per 10 vL. To the mixture, CPP01 or MIP01 was added in an amount of 10 μg. An adjuvant-free administration solution containing the antigen alone was also prepared as a control.

The administration solutions prepared as described above (Table 3) were each administered in an amount of 10 μL to the nasal cavity (5 μL to each nostril) of a BALE/c mouse (female, five-week-old) twice at an interval of three weeks (five mice per group). The whole blood was collected two weeks after each administration, and centrifuged to prepare serum. After the collection of blood two weeks after the second administration, the nasal cavity was washed with 400 μL of protease inhibitor-containing D-PBS per individual, and the wash was collected as a nasal cavity wash. The serum was used for measurement of the titer of IgG specifically bound to A/Singapore/GP1908/2015 strain and B/Maryland/15/2016 strain (total IgG), and the nasal cavity wash was used for measurement of the titer of IgA specifically bound to A/Singapore/GP1908/2015 strain and B/Maryland/15/2016 strain.

TABLE 3

| # | Antigen Subtype/ lineage | Dose (μgHA/strain/shot) | Adjuvant Name | Sequence (N-terminal → C-terminal) | Dose (μg/shot) |
|---|---|---|---|---|---|
| 7 | A/H1N1 | 1 | CPP01 | GRKKRRQRRRPPQ | 10 |
| 8 | A/H1N1 | 1 | MIP01 | GRKKRRQRRRPPQ-G3PNA | 10 |
| 9 | A/H1N1 | 1 | — | — | — |
| 10 | B/Victoria | 1 | CPP01 | GRKKRRQRRRPPQ | 10 |
| 11 | B/Victoria | 1 | MIP01 | GRKKRRQRRRPPQ-G3PNA | 10 |
| 12 | B/Victoria | 1 | — | — | — |

Figure 3A:
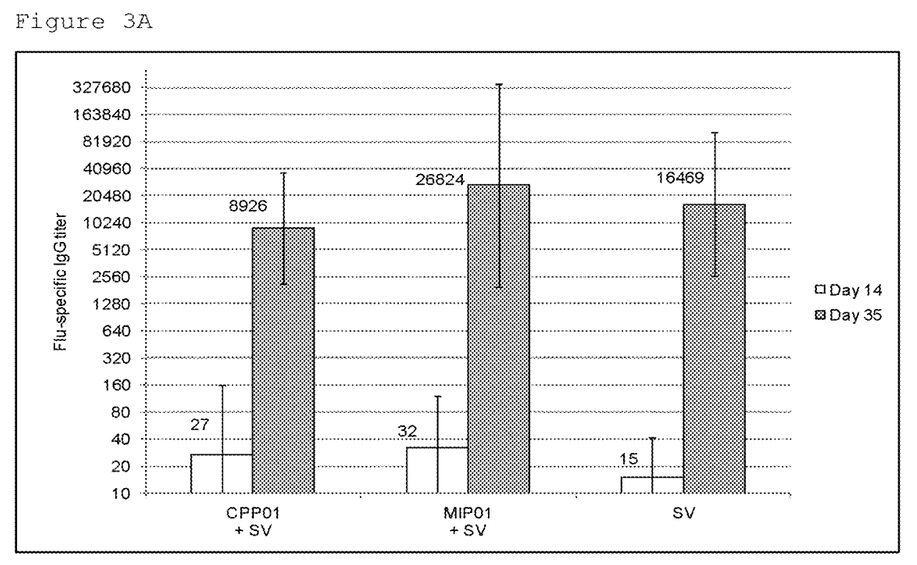
FIG. 3A shows an IgG antibody titer against A/Singapore/GP1908/2015 strain in transnasal administration.
Figure 3B:
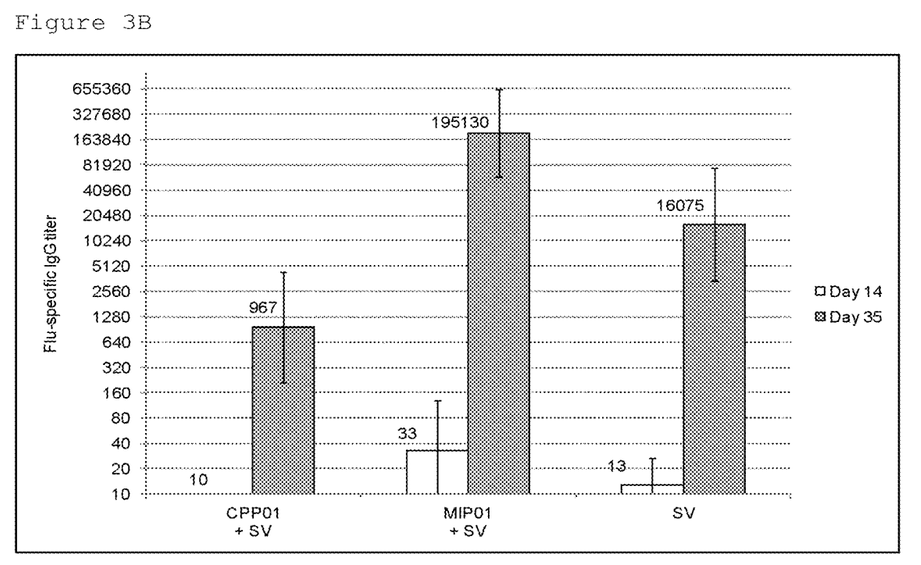
FIG. 3B shows an IgG antibody titer against B/Maryland/15/2015 strain in transnasal administration.
Figure 4A:
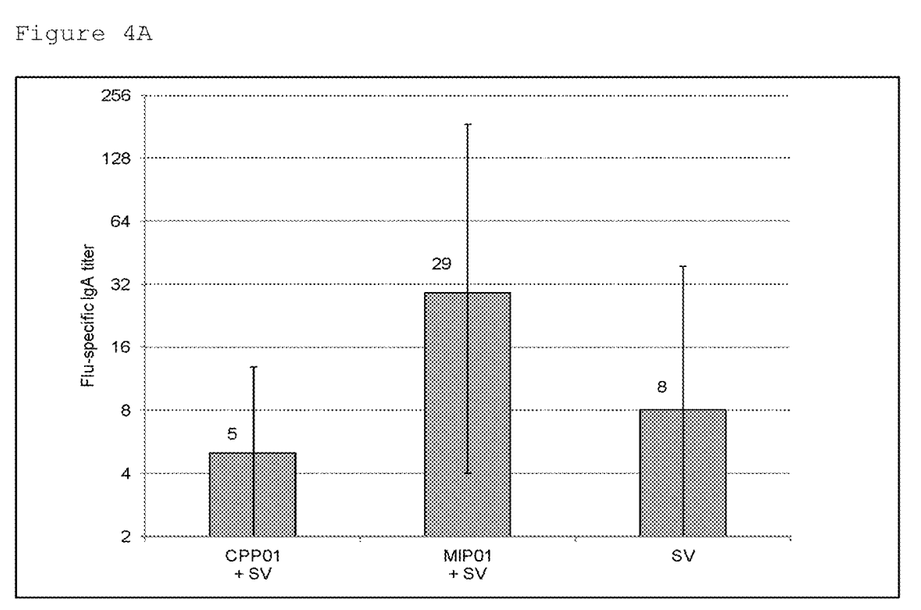
FIG. 4A shows an IgA antibody titer against A/Singapore/GP1908/2015 strain in a nasal wash in transnasal administration.
Figure 4B:
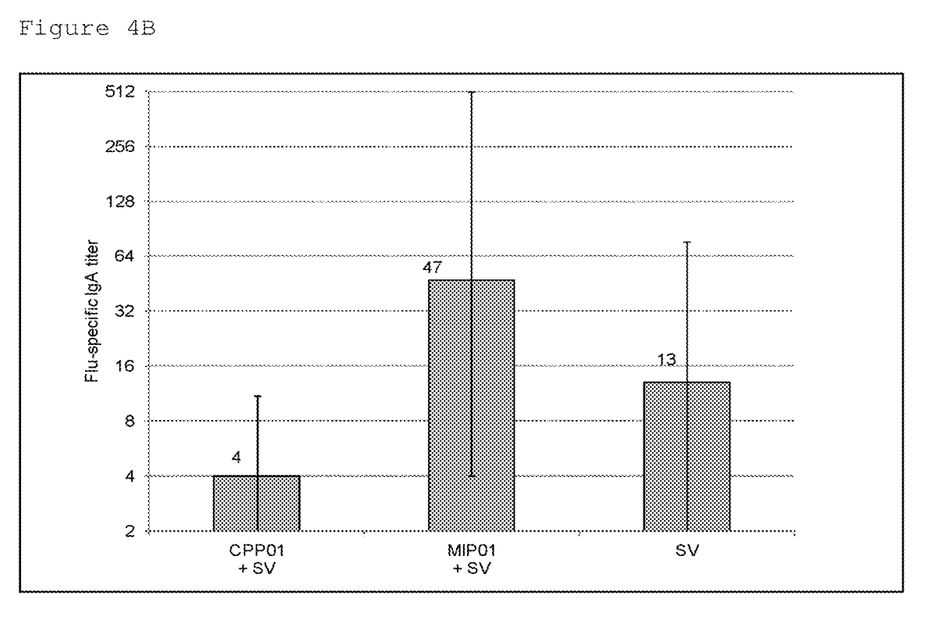
FIG. 4B shows an IgA antibody titer against B/Maryland/15/2015 strain in a nasal wash in transnasal administration.

The results of the IgG titer against each strain are as shown in FIGS. 3A and 3B, and also in the transnasal administration, the blood antigen-specific IgG titer against each strain was higher as compared to that in the adjuvant-free group in both the first and second administrations. Particularly for the IgG titer against B/Maryland/15/2016 strain, a significant increase in antibody titer with respect to the adjuvant-free group was observed (Mann-Whitney U test, $p<0.05$). For the antigen-specific IgA titer in the nasal cavity wash, the IgA titer against each strain was the highest in the MIP01 administration group, the next-highest in the adjuvant-free group and the lowest in the CPP01 administration group at both the administrations (FIGS. 4A and 4B). Therefore, MIP in which a peptide nucleic acid is modified with a cell penetrating peptide is considered to have adjuvant activity not only in administration by injection but also in transmucosal administration and to promote IgA induction in the mucosal membrane in addition to IgG induction in the blood in the transmucosal administration.

Example 3: Natural Immunity Activating Capability of MIP03

The natural immunity activating capability of MIP03 was evaluated in vitro.

To cells of Raw 264.7 Reporter Cell Line (Novus biologicals, NBP 2-26261) at $1\times10^6$ cells/mL, MIP03 was added at a final concentration of 10, 20, 40 or 80 µM. The mixture was cultured at 37° C., 5% $CO_2$ for 2 days, and the culture fluid was then collected. The collected culture fluid was centrifuged at 12,000×g for 1 minute, and alkaline phosphatase and cytokine in the supernatant were measured. SEAP Reporter Gene Assay Kit Luminescence (Cayman Chemical, 600260) was used for measurement of alkaline phosphatase, and Bio-Plex Pro Mouse Cytokine GI23-Plex (Bio-Rad, M60009RDPDB03) was used for measurement of cytokine. A culture medium was added as a negative control (NC), Imiquimod (0.02 IM) which is an agonist of Toll-like receptor 7 was added as a positive control in measurement of cytokine, and evaluation was performed by comparison with these controls.

Figure 5:
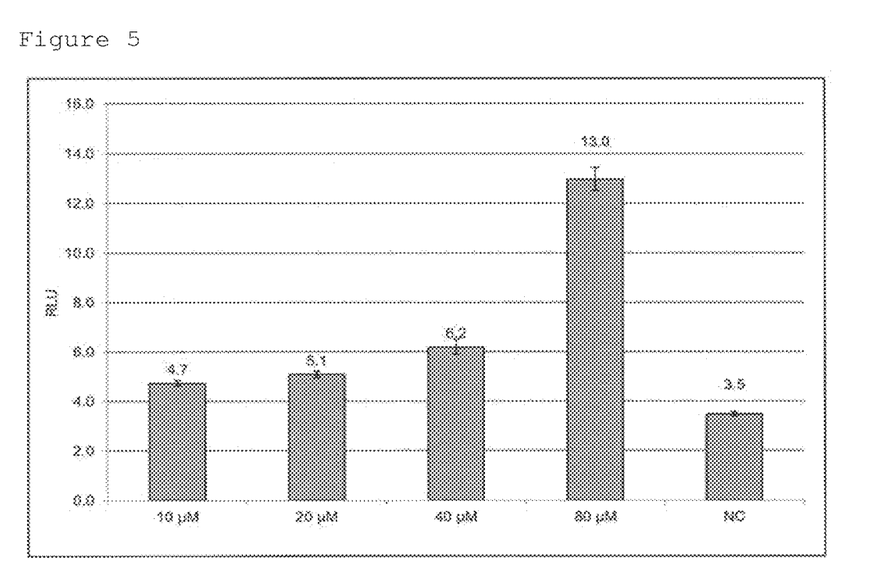
FIG. 5 shows an activating action of MIP03 on NFκB.
Figure 6:
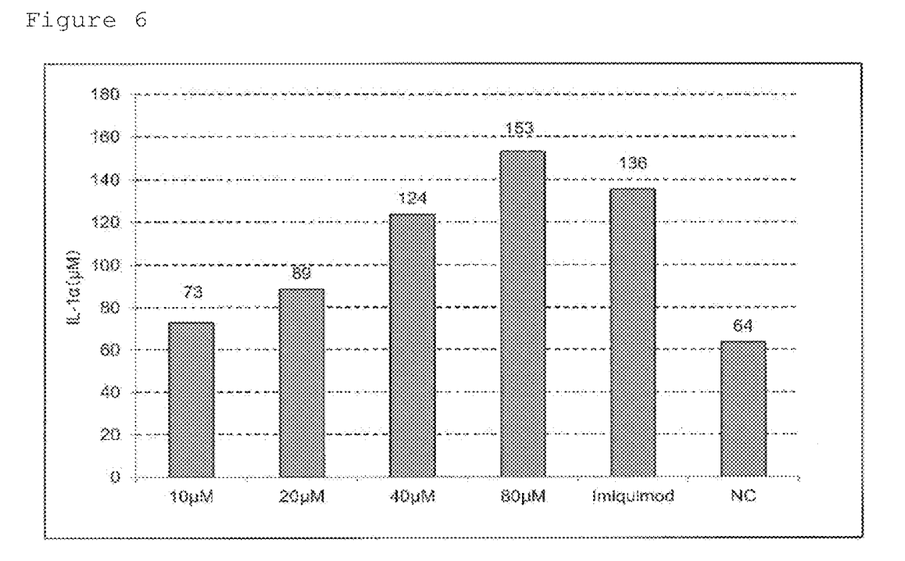
FIG. 6 shows a cytokine (IL-1α) inducing action of MIP03.
Figure 7:
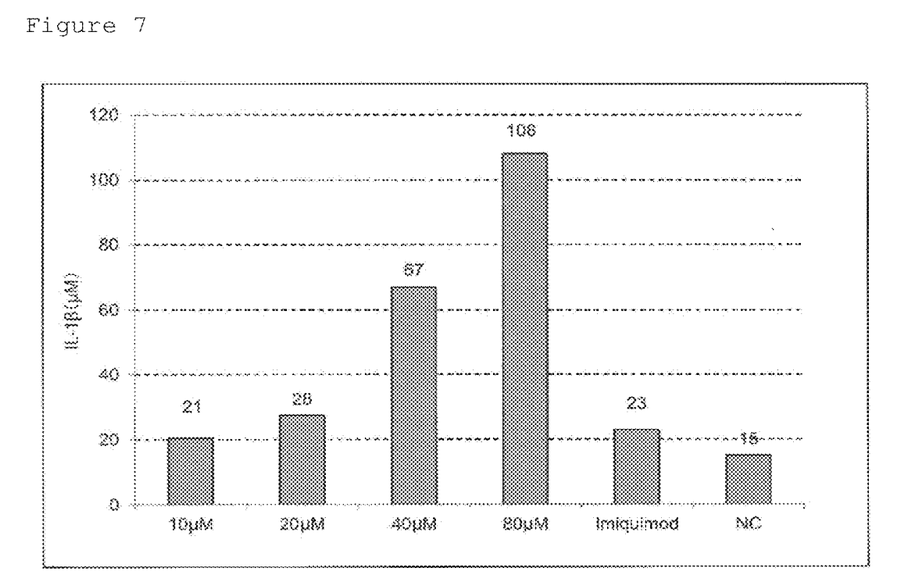
FIG. 7 shows a cytokine (IL-1β) inducing action of MIP03.
Figure 8:
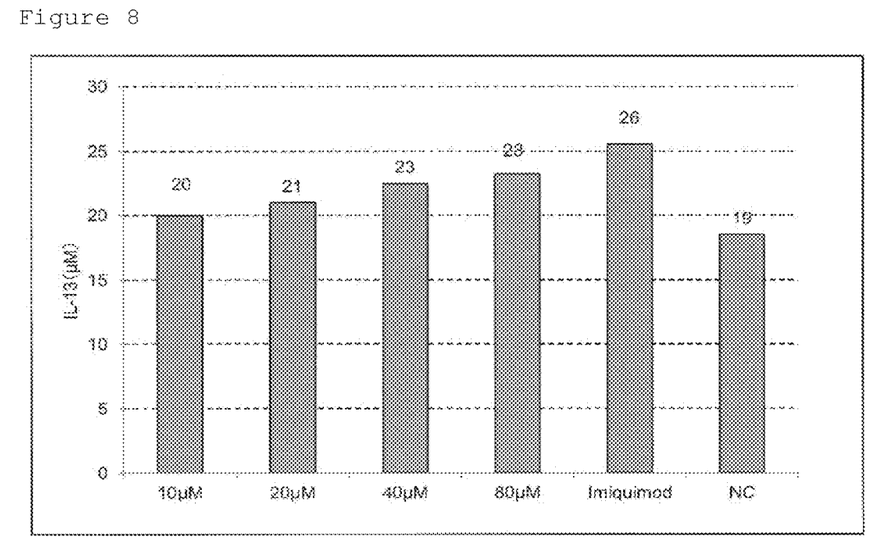
FIG. 8 shows a cytokine (IL-13) inducing action of MIP03.
Figure 9:
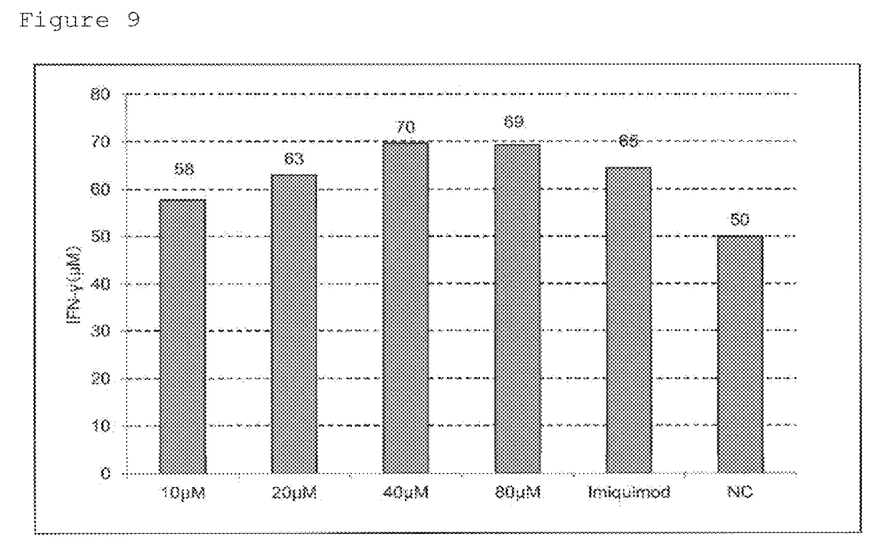
FIG. 9 shows a cytokine (IFN-γ) inducing action of MIP03.

The results of measuring alkaline phosphatase are as shown in FIG. 5. There was observed an improvement in luminescence signals of alkaline phosphatase dependent on the concentration of MIP03 added. Therefore, MIP03 was shown to promote activation of NFκB, suggesting that MIP03 activates natural immunity. FIGS. 6 to 9 show the results of measuring cytokine. There was observed an increase in induction of IL-1α and IL-1β dependent on the concentration of MIP03 (FIGS. 6 and 7), and particularly for IL-1β, very high induction was observed as compared to Imiquimod (FIG. 7). As to Th2- and 1-related cytokines, FIG. 8 shows the results of measuring IL-13 and FIG. 9 shows the results of measuring IFN-γ. For both the cytokines, induction equivalent to that by Imiquimod which is a positive control was observed.

As described above, MIP03 activates NFκB and has a high capability of inducing IL-1β, and therefore MIP03 is likely to promote activation of the natural immune system via the C-type lectin receptor and the Nod-like receptor, and is resultantly considered to exhibit a capability of inducing Th1/Th2 cytokines relating to an antibody response. Thus, MIP is an adjuvant having a capability of activating natural immunity.

The invention claimed is:

1. An adjuvant comprising a peptide nucleic acid to which a cell penetrating peptide is bound,
wherein the peptide nucleic acid is represented by the following formula (1):

$$\text{(1)}$$

wherein Base is independently guanine or cytosine,
wherein R represents —COOH or —CONH$_2$,
wherein n represents an integer of 1 to 10, and
wherein a C-terminus of the cell penetrating peptide is bound to a terminal amine group in formula (I) of the peptide nucleic acid.

2. The adjuvant according to claim 1, wherein the cell penetrating peptide is selected from the group consisting of peptides consisting; of amino acid sequences set forth as SEQ ID NOS: 1 to 7.

3. The adjuvant according to claim 1, wherein the cell penetrating peptide consists of an amino acid sequence set forth as SEQ ID NO: 1.

4. The adjuvant according to claim 1, wherein n is an integer of 1 to 8.

5. The adjuvant according to claim 1, wherein R is —CONH$_2$.

6. A vaccine composition comprising the adjuvant according to claim 1, and an antigen.

7. The adjuvant of claim 1, wherein Base are all only guanine or all only cytosine.

* * * * *

SEQUENCE LISTING

```
<160> NUMBER OF SEQ ID NOS: 7

<210> SEQ ID NO 1
<211> LENGTH: 13
<212> TYPE: PRT
<213> ORGANISM: Human immunodeficiency virus

<400> SEQUENCE: 1

Gly Arg Lys Lys Arg Arg Gln Arg Arg Arg Pro Pro Gln
1               5                   10

<210> SEQ ID NO 2
<211> LENGTH: 16
<212> TYPE: PRT
<213> ORGANISM: Unknown
<220> FEATURE:
<223> OTHER INFORMATION: Penetratin; Origin Drosophila Antennapedia

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Designed peptide

<400> SEQUENCE: 3

Arg Arg Arg Arg Arg Arg Arg Arg
1               5

<210> SEQ ID NO 4
<211> LENGTH: 9
<212> TYPE: PRT
```

```
<213> ORGANISM: Artificial Sequence
<220> FEATURE:
<223> OTHER INFORMATION: Designed peptide

<400> SEQUENCE: 4

Arg Arg Arg Arg Arg Arg Arg Arg Arg
1               5

<210> SEQ ID NO 5
<211> LENGTH: 27
<212> TYPE: PRT
<213> ORGANISM: Homo sapiens

<400> SEQUENCE: 5

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 6
<211> LENGTH: 20
<212> TYPE: PRT
<213> ORGANISM: Simian virus 40

<400> SEQUENCE: 6

Lys Glu Thr Trp Trp Glu Thr Trp Trp Thr Glu Trp Ser Gln Pro Lys
1               5                   10                  15

Lys Arg Lys Val
            20

<210> SEQ ID NO 7
<211> LENGTH: 38
<212> TYPE: PRT
<213> ORGANISM: Homo sapiens

<400> SEQUENCE: 7

Leu Leu Gly Asp Phe Glu Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35
```